US010436724B2

(12) United States Patent
Grimshaw et al.

(10) Patent No.: US 10,436,724 B2
(45) Date of Patent: Oct. 8, 2019

(54) SYSTEM AND METHOD FOR QUANTIFYING X-RAY BACKSCATTER SYSTEM PERFORMANCE

(71) Applicant: The Boeing Company, Chicago, IL (US)

(72) Inventors: Matthew T. Grimshaw, Seattle, WA (US); Talion Edwards, Wentzville, MO (US); Gary E. Georgeson, Tacoma, WA (US); Daniel J. Wright, Mercer Island, WA (US); James E. Engel, Newport Beach, CA (US); Morteza Safai, Newcastle, WA (US); Yuan-Jye Wu, Issaquah, WA (US); Taisia Tsukruk Lou, St. Louis, MO (US); Rodney S. Wright, Huntington Beach, CA (US)

(73) Assignee: The Boeing Company, Chicago, IL (US)

( * ) Notice: Subject to any disclaimer, the term of this patent is extended or adjusted under 35 U.S.C. 154(b) by 428 days.

(21) Appl. No.: 15/184,644

(22) Filed: Jun. 16, 2016

(65) Prior Publication Data

US 2017/0227478 A1    Aug. 10, 2017

Related U.S. Application Data

(63) Continuation of application No. 14/269,930, filed on May 5, 2014, now Pat. No. 9,398,676.

(51) Int. Cl.
*G01N 23/00* (2006.01)
*G01N 23/203* (2006.01)
(Continued)

(52) U.S. Cl.
CPC ......... *G01N 23/203* (2013.01); *G01V 5/0025* (2013.01); *H05G 1/26* (2013.01);
(Continued)

(58) Field of Classification Search
CPC .......................... G01N 23/203; G01V 5/0025
See application file for complete search history.

(56) References Cited

U.S. PATENT DOCUMENTS 7,463,714 B2    12/2008  Edwards et al.
7,508,910 B2     3/2009  Safai et al.
(Continued)

OTHER PUBLICATIONS

U.S., Restriction Requirement; U.S. Appl. No. 14/269,930 (dated Dec. 1, 2015).
(Continued)

*Primary Examiner* — Dani Fox
(74) *Attorney, Agent, or Firm* — Vivacqua Law

(57) ABSTRACT

A system for quantifying x-ray backscatter system performance may include a support; a plurality of rods mounted on the support; the rods of the plurality of rods arranged parallel to each other, having generally curved outer surfaces, and being arranged in groups of varying widths, each group of the groups having at least two of the rods of a same width; and a user interface configured to be connected to receive a backscatter signal from an x-ray backscatter detector associated with an x-ray tube, apply a transfer function to generate a transfer curve representing x-ray backscatter for each rod of the plurality of rods from x-rays transmitted by the x-ray tube.

20 Claims, 17 Drawing Sheets

(51) Int. Cl.
*H05G 1/26* (2006.01)
*G01V 5/00* (2006.01)

(52) U.S. Cl.
CPC . *G01N 2223/303* (2013.01); *G01N 2223/408* (2013.01); *G01N 2223/631* (2013.01)

(56) References Cited

U.S. PATENT DOCUMENTS

| | | | |
|---|---|---|---|
| 7,529,343 B2 | 5/2009 | Safai et al. | |
| 7,599,471 B2 | 10/2009 | Safai et al. | |
| 7,623,626 B2 | 11/2009 | Safai et al. | |
| 7,649,976 B2 | 1/2010 | Georgeson et al. | |
| 8,033,724 B2 | 10/2011 | Edwards et al. | |
| 8,094,781 B1 | 1/2012 | Safai et al. | |
| 2010/0034347 A1* | 2/2010 | Rothschild | G01V 5/0025 378/19 |
| 2010/0327174 A1* | 12/2010 | Edwards | G01N 23/203 250/370.09 |

OTHER PUBLICATIONS

U.S., Notice of Allowance; U.S. Appl. No. 14/269,930 (dated Mar. 16, 2016).

* cited by examiner

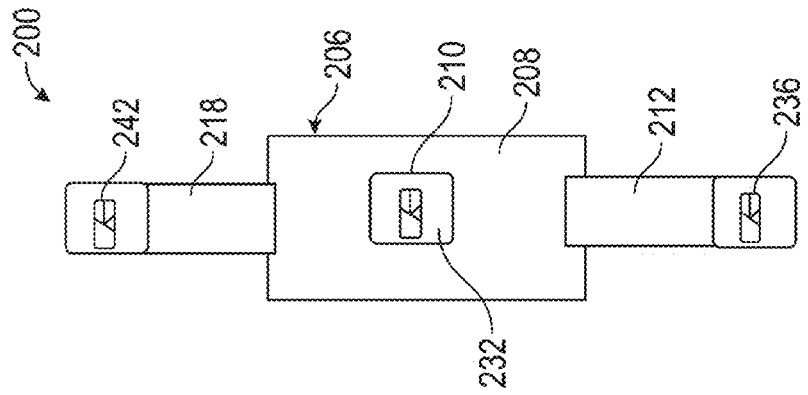
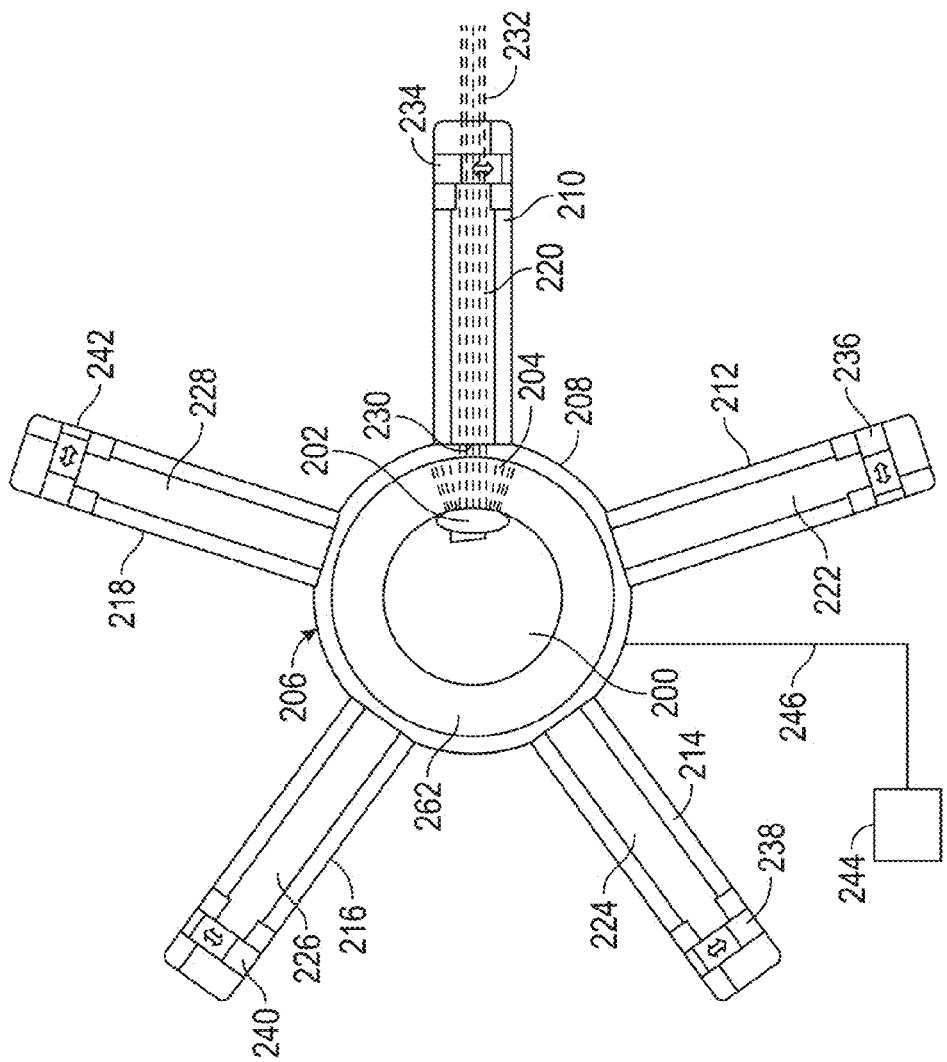

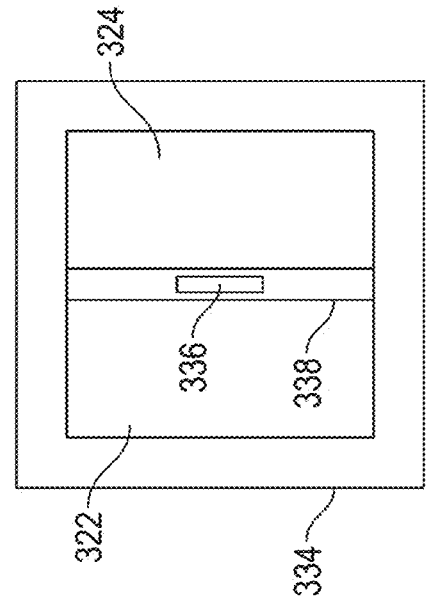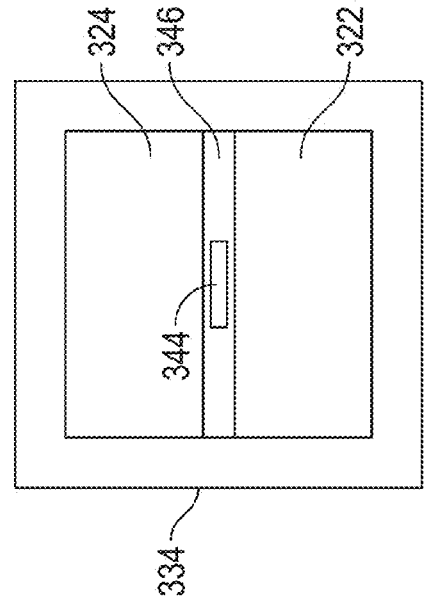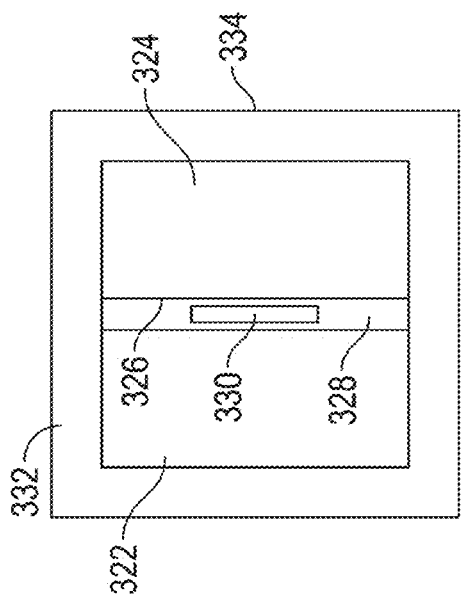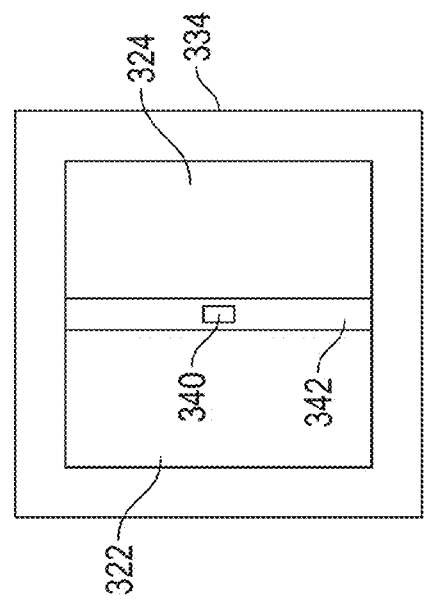

SYSTEM AND METHOD FOR QUANTIFYING X-RAY BACKSCATTER SYSTEM PERFORMANCE

STATEMENT OF GOVERNMENT RIGHTS

This invention was made with United States Government support under Contract No. N00019-11-G-0001 awarded by the Department of Defense. The United States Government has certain rights in this invention.

TECHNICAL FIELD

The disclosure relates to devices for measuring the performance of x-ray imaging systems and, more particularly, to devices and methods for quantifying the performance of x-ray backscatter imaging systems.

BACKGROUND

It is often necessary to inspect structural components of large objects, such as aircraft, maritime vessels, automobiles, and other large investment assemblies, for defects and damage. Other structural objects that may require inspection include petrochemical facilities, power generation facilities, nuclear facilities, water treatment facilities, and the like.

Inspection of such structures and facilities by partial or complete disassembly of the structures to visually inspect internal components of interest may be impracticable because it is too time-consuming and expensive. In some instances it may not be possible to inspect the desired component without partially destroying the component of interest. Further, transportation of such structures and components of large object or facilities to an inspection location may be difficult, expensive, and in some instances impossible.

A technique for inspecting such components is the use of x-ray imaging. Inspection by x-ray imaging requires an x-ray transmitter that transmits x-rays sufficiently powerful to pass through the object of interest and its surrounding components to be detected by a film or other detection means. Such devices are large, cumbersome and relatively expensive.

X-ray backscattering systems provide an inspection process in which x-rays are reflected from the object or component of interest and recorded by a detector or detectors. X-ray backscattering systems do not need to be powerful enough to transmit x-rays entirely through the component of interest and its surrounding components. Rather, partial penetration is all that is required. X-ray backscatter inspection systems are smaller, more portable, and less expensive than traditional x-ray imaging systems.

A problem with x-ray backscattering systems is that the reference standard used for calibrating or adjusting traditional through-transmission film or digital x-rays does not work for x-ray backscatter systems. Scattered x-rays off of the standards or gauges used for traditional through-transmission x-ray inspection do not provide relevant spatial frequency information because x-rays are scattered differently (i.e., with respect to intensity and angle) from different types of materials. Accordingly, there is a need for a method and system for quantifying x-ray backscatter system performance.

Further, in order to image very small features or detect small cracks, such as stress corrosion cracks, the size of the openings in the aperture of an x-ray backscatter device must be very small, on the order of 0.25 millimeters (mm) or 0.5 mm in diameter. However, with such small apertures, the amount of x-ray flux that is emitted from the x-ray tube is very low, which requires a relatively slow x-ray tube scan speed and a relatively small scan area for each raster scan, so that many more raster scans are required for a given inspection area.

Often, x-ray tubes with relatively larger apertures may be used for general scanning because they permit higher x-ray flux, which enables a relatively larger area to be scanned for each pass, and at a faster scan rate. However, switching between large and small apertures takes time and requires multiple sets of apertures of different sizes. Another disadvantage is that smaller apertures are more difficult and expensive to fabricate than larger apertures. The dimensions of small apertures make reproducibility of apertures difficult and require software normalization to achieve consistent flux intensities from the x-ray tube.

SUMMARY

The disclosure describes a system and method for quantifying x-ray backscatter system performance that overcomes the disadvantages of prior systems for testing x-ray backscatter system performance, especially prior test systems adapted from calibrating or adjusting traditional through-transmission film or digital x-rays. The disclosed system is highly portable and therefore can be transported to the site of the apparatus under test. In one embodiment, a system for quantifying x-ray backscatter system performance includes a support; a plurality of rods mounted on the support; the rods of the plurality of rods arranged parallel to each other, having generally curved outer surfaces, and being arranged in groups of varying widths, each group of the groups having at least two of the rods of a same width; and a user interface configured to be connected to receive a backscatter signal from an x-ray backscatter detector associated with an x-ray tube, apply a transfer function to generate a transfer curve representing x-ray backscatter for each rod of the plurality of rods from x-rays transmitted by the x-ray tube.

In another embodiment, an x-ray backscatter system includes an x-ray tube for emitting an x-ray field; an enclosure surrounding the x-ray tube blocking the x-ray field; and the enclosure having an aperture positioned to allow x-rays to exit the enclosure in a relatively narrow x-ray beam, the aperture being adjustable in one or both of preselected size of opening and preselected shape, whereby an amount of x-ray flux through the aperture is varied.

Other objects and advantages of the disclosed system and method for quantifying x-ray backscatter system performance will be apparent from the following description, the accompanying drawings, and the appended claims.

BRIEF DESCRIPTION OF THE DRAWINGS

FIGS. 9A and 9B show side elevation in section and end elevation, respectively, of an aperture wheel having the disclosed adjustable apertures;

FIGS. 15A, 15B, 15C, and 15D show plan views of another embodiment of the disclosed adjustable aperture mounted in an end of a square collimator;

DETAILED DESCRIPTION

Figure 1:
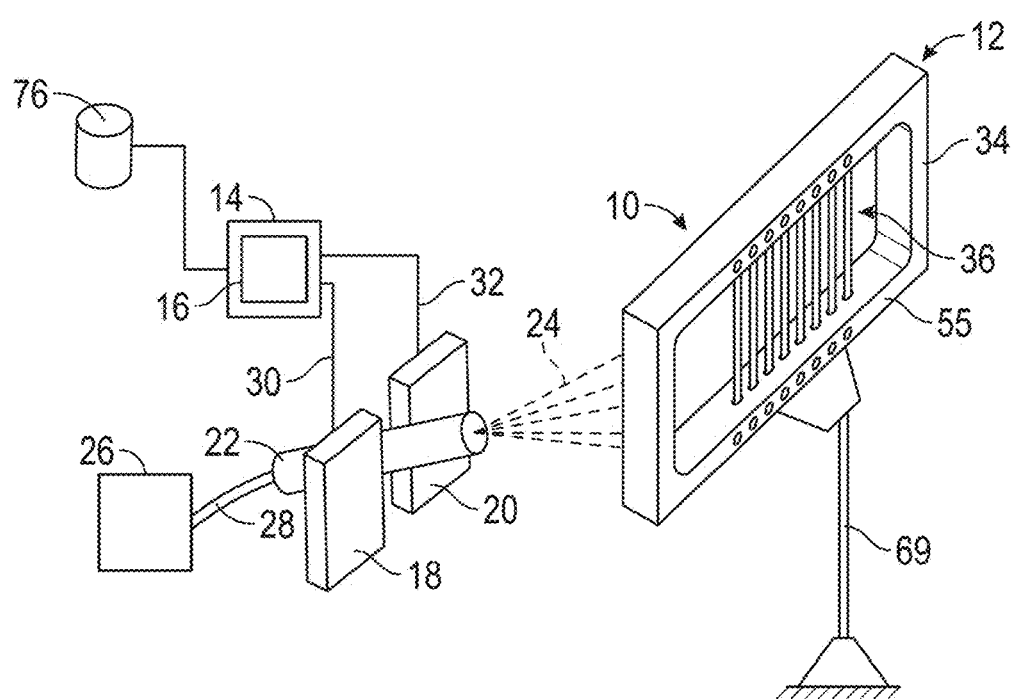
FIG. 1 is a schematic perspective view of the system for quantifying x-ray backscatter system performance.

The system for quantifying x-ray backscatter system performance is shown in FIG. 1 and generally designated 10. The system 10 may include a modulation transfer function ("MTF") standard 12 and a display 14 that may include a user interface, such as a graphical user interface ("GUI") 16. The display 14 may receive a signal from x-ray backscatter detectors 18, 20, which in an embodiment may be solid state detectors, associated with an x-ray tube 22, which in an embodiment may be a small filament micro-focus x-ray tube. An x-ray tube 22 in the form of a small filament micro-focus x-ray tube may be preferable in some applications because a small filament micro-focus x-ray tube may be lighter and smaller in size than the x-ray tube of a conventional x-ray backscatter system, possesses a relatively smaller x-ray field of view 24, and may be relatively low in radiation leaking. The x-ray tube 22 may be connected to a source of electrical power 26 by power cables 28. In an embodiment, power cables 28 may also supply power to the detectors 18, 20 and/or to display 14. The display 14 may receive signals from the detectors over cables 30, 32, respectively.

Figure 2:
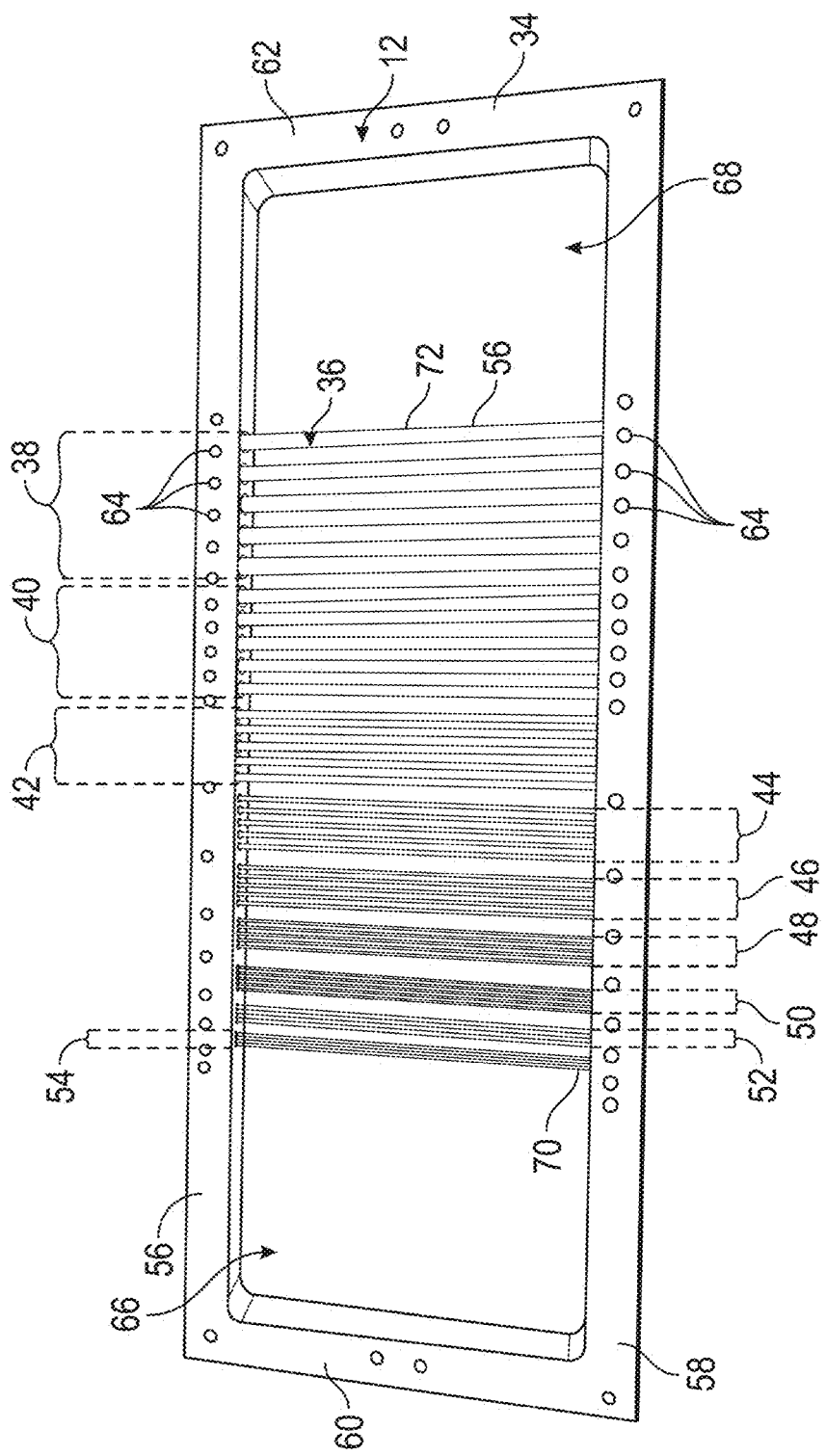
FIG. 2 is a front elevation of the modulation transfer function standard of the system of FIG. 1.

As shown in FIGS. 1 and 2, the MTF standard 12 may include a support 34 in the form of a frame 55, which in an embodiment may be made of aluminum channel, and in a specific embodiment square aluminum channel. A plurality of rods, generally designated 36, may be mounted on the support 34 and arranged parallel to each other. The individual rods 56 of the plurality of rods 36 may have generally curved outer surfaces, and may be arranged in groups 38, 40, 42, 44, 46, 48, 50, 52, 54 of varying widths. In an embodiment, the rods 56 may be arranged in groups 38-54 in which the rods 56 have a common width. Thus, the five rods 56 comprising group 38 may be of a common width, the five rods comprising group 40 may have a common width that is different from the width of the rods in group 38 (in an embodiment, the width may be less than the rods of group 38), the five rods comprising group 42 may have a width that is different from the widths of the rods in groups 40 and 38 (in an embodiment, the width may be less than the rods of group 40), the five rods comprising group 44 may have a width that differs from the widths of the rods in groups 42, 40 and 38 (in an embodiment, the width may be less than the width of the rods in group 42), and so on for the remaining groups of rods 46, 48, 50, 52, 54.

In embodiments, groups of rods 38-54 may have greater or fewer rods 56 of a common diameter in each group than the five rods per group depicted in FIG. 2. In other embodiments, the numbers of rods 56 may vary from group to group in the groups 38-54. In still other embodiments, the standard 12 may include groups (not shown) of rods 36 in addition to the groups 38-54 that may be thicker or wider than the rods of group 38, thinner or narrower than the rods of group 54, or both.

In an embodiment, the rods 36 may be arranged in parallel in a common plane on the support 34. In an embodiment, the curved rods 36 may be round or circular in cross-section. In an embodiment, the rods 36 may be made of a polymer or other hydrocarbon material, such as nylon 12. Use of rods 36 that are made of a polymer and that are round or circular in cross-section may be preferable because the composition and shape may provide maximum backscattering from the MTF standard 12. As shown in FIG. 2, in an embodiment, the rods 56 of each of the groups 38-52 of the plurality of rods 36 may be spaced evenly from each other. In an embodiment, the rods 56 of each of the groups 38-54 may be spaced from each other a distance equal to, or approximately equal to, the width of the rods in each of the groups.

As shown in FIG. 2, the support 34 of the MTF standard 12 may include a frame 55 having a pair of opposing side rails 57, 58 and a pair of opposing end rails 60, 62. In an embodiment, the frame 55 may be generally rectangular, such that the side rails 57, 58 are generally parallel to each other, and the end rails 60, 62 are parallel to each other. The rods 56 may be mounted on the frame 55 to extend between the pair of opposing side rails 57, 58. In an embodiment, the rods 56 may be secured within the frame 55 by set screws 64 so that the rods may be properly tensioned on the frame. In a particular embodiment, the spaces 66-68 between each end rail 60, 62, respectively of the pair of opposing end rails and a next adjacent one of the rods 70, 72, respectively, is greater than a spacing between the rods 36. This increased separation may avoid backscatter caused by the end rails 60, 62.

Although the MTF standard 12 may be positioned at an angle relative to the x-ray tube, it is preferable to position the MTF standard such that the support 34 positions the plurality of rods 36 perpendicular, or substantially perpendicular, to the x-ray field of view 24 transmitted by the x-ray tube 22. This may be effected by mounting the support 34 on a stand 69, which in embodiments may be adjustable to raise and lower the MTF standard 12 as well as pivot the standard relative to the x-ray tube 22 and backscatter detectors 18, 20. It also may be preferable to arrange the rods 56 on the support 34 in a sequence progressing from rods having a relatively large thickness, such as the rods of group 38, to progressively thinner rods in groupings 40-54, in which each of the next grouping of rods has a thinner diameter than the rods to the right of it (as shown in FIG. 2). Thus, the groups of rods 38-54 are arranged on the support 34 in a sequence progressing from a relatively large thickness to a relatively small thickness.

The display 14 may be configured to be connected to receive a backscatter signal from x-ray backscatter detectors 18, 20 associated with the x-ray tube 22 and generate a display on GUI 16 representing photon counts of x-ray backscatter for each rod 56 of the plurality of rods 36 from x-rays transmitted by the x-ray tube 22.

Figure 3:
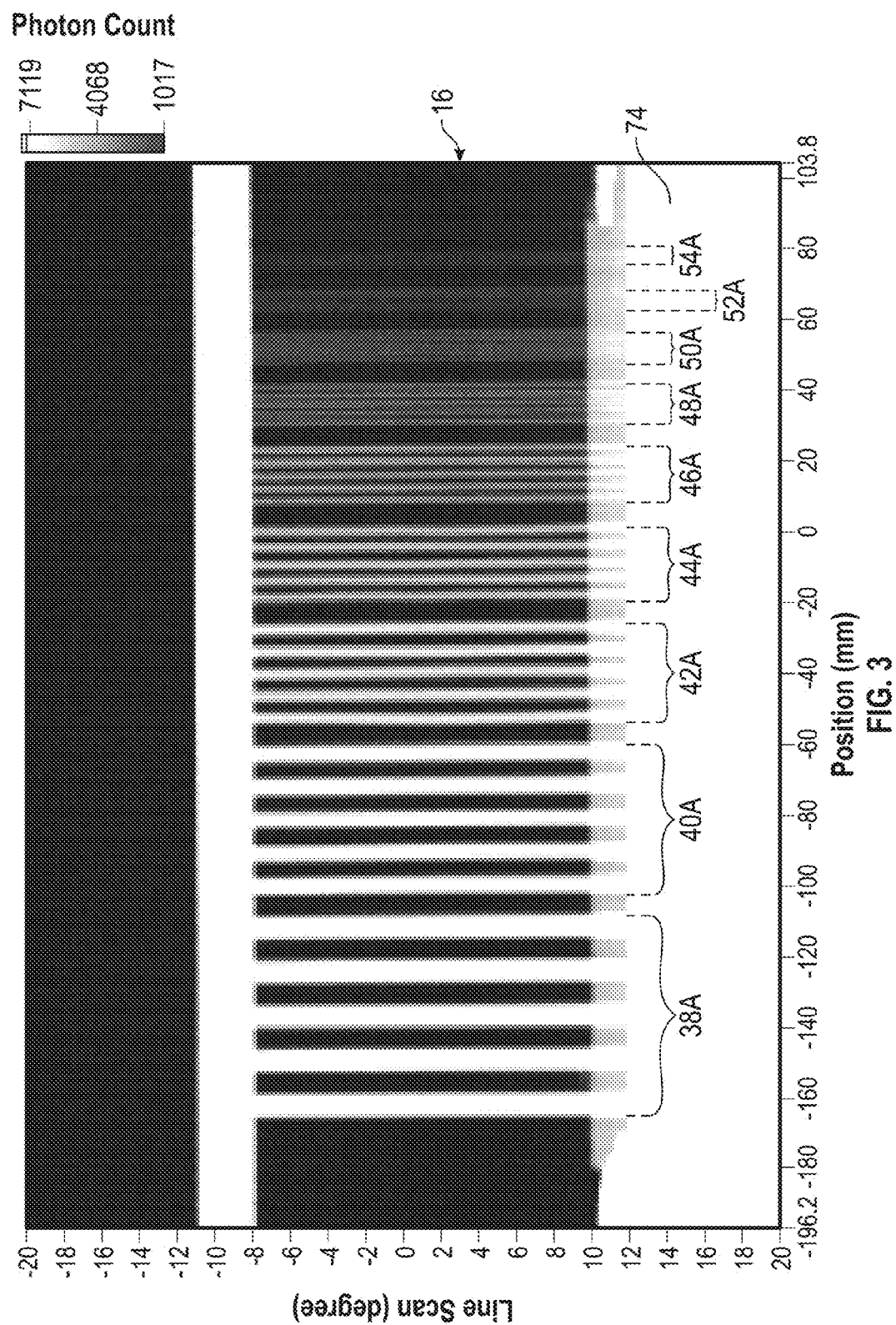
FIG. 3 is a display of a backscatter image of the modulation transfer function standard of FIG. 2.

As shown in FIG. 3, the user interface 16 may display a backscatter image 74 that may be received from either one of the detectors 18, 20 (FIG. 1). The x-ray backscatter images from the rods 56 of group 38 (FIG. 2) are shown as group 38A, the backscatter from the rods of group 40 are shown as grouping 40A, the rods of group 42 are shown as group 42A, and so on for backscatter images 44A, 46A, 48A, 50A, 52A and 54A, which correspond to groups 44-54, respectively. The x-ray backscatter images for the thicker rods, such as the rods of groups 38, 40, 42 appear on the image 74 relatively sharply defined as groupings 38A, 40A and 42A. In contrast, the groupings of the progressively thinner rods of 44-54 (FIG. 2) are relatively less defined, and are faint and blurry, such as for groupings 44A, 46A, and 48A, whereas the images 50A, 52A and 54A may appear quite faint. Thus, the MTF reference standard 12 provides a spectrum over which the sensitivity of the detectors 18, 20 may be measured. In an embodiment, the image of FIG. 3 may be stored in storage 76 connected to display 14 (FIG. 1).

Figure 4:
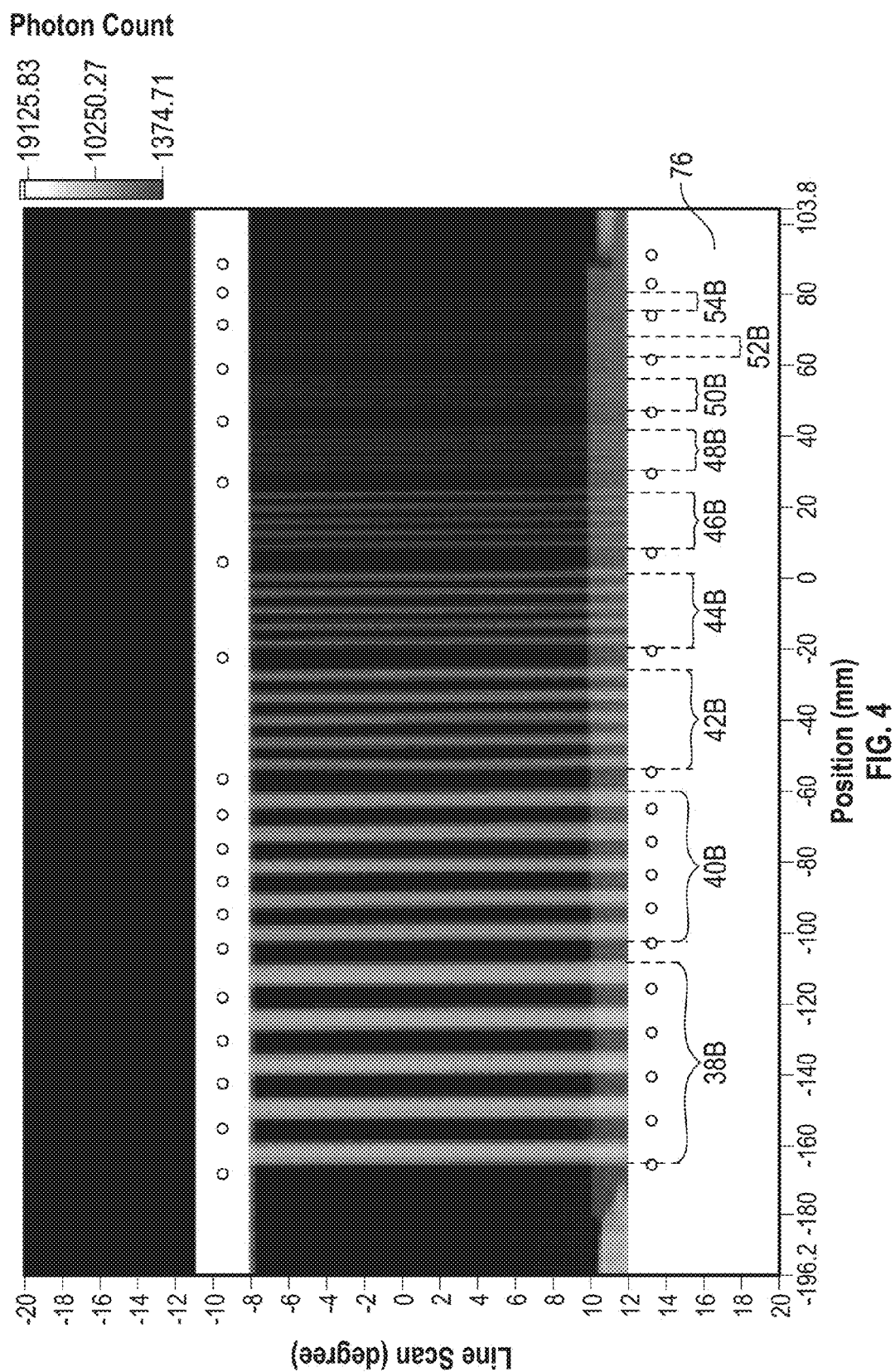
FIG. 4 is a display of a second backscatter image of the modulation transfer function standard of FIG. 2.

The image 74 may be stored in storage 76 as a reference image. As shown in FIG. 4, image 77 shows x-ray backscatter images of groups 38B, 40B, 42B, 44B, 46B, 48B, 50B, 52B, and 54B corresponding to x-ray backscatter from rod groups 38-54, respectively of the MTF standard 12. Images 38B-54B are fainter and less sharp than their counterpart images 38A-54A of image 74. Backscatter images for groups 48B-54B may be barely visible, indicating a much lower photon count detected by detector 18 and/or 20. This may indicate an out-of-adjustment or out of alignment condition for the x-ray tube 22 and detectors 18, 20 (FIG. 1).

Figure 5:
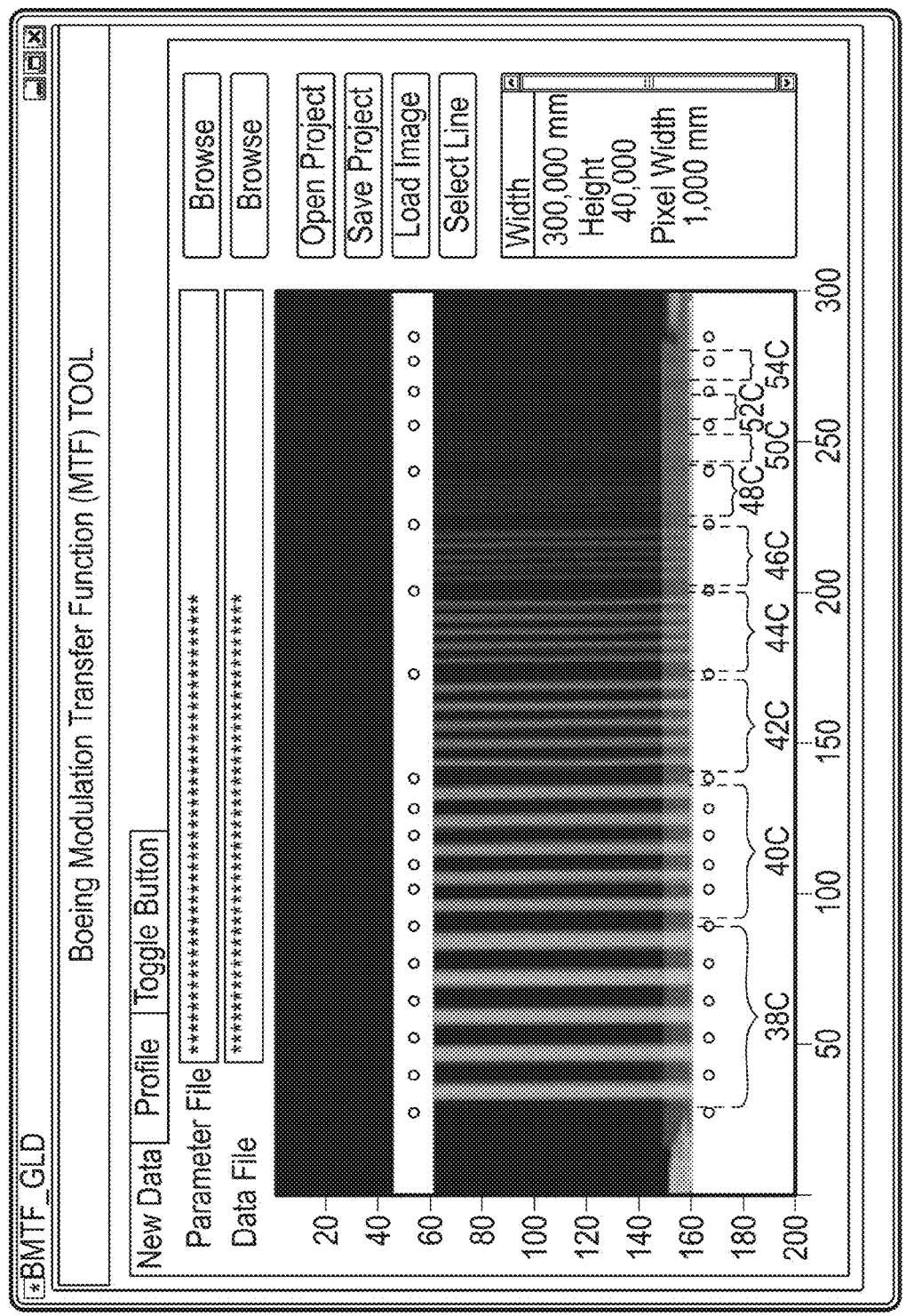
FIG. 5 is a display of a backscatter image of the modulation transfer function standard from two detectors of the system of FIG. 1, utilizing a graphical user interface of the system of FIG. 1.

As shown in FIG. 5, the GUI 16 (FIG. 1) of the display 14 may show a screenshot of the x-ray backscatter image 78 of the reference standard 12 that is comprised of scans from both detectors 18, 20. The image shows the combined backscatter images of the group 38 of rods 36 (FIG. 2), shown as group 38C, the combined images of group 40 shown as images 40C, and so on for groups 42-56, shown as images 42C, 44C, 46C, 48C, 50C, 52C, and 54C. Again, the images 38C-54C may be fainter and less sharp than the reference images 38A-54A of display image 74 of FIG. 3.

Figure 6:
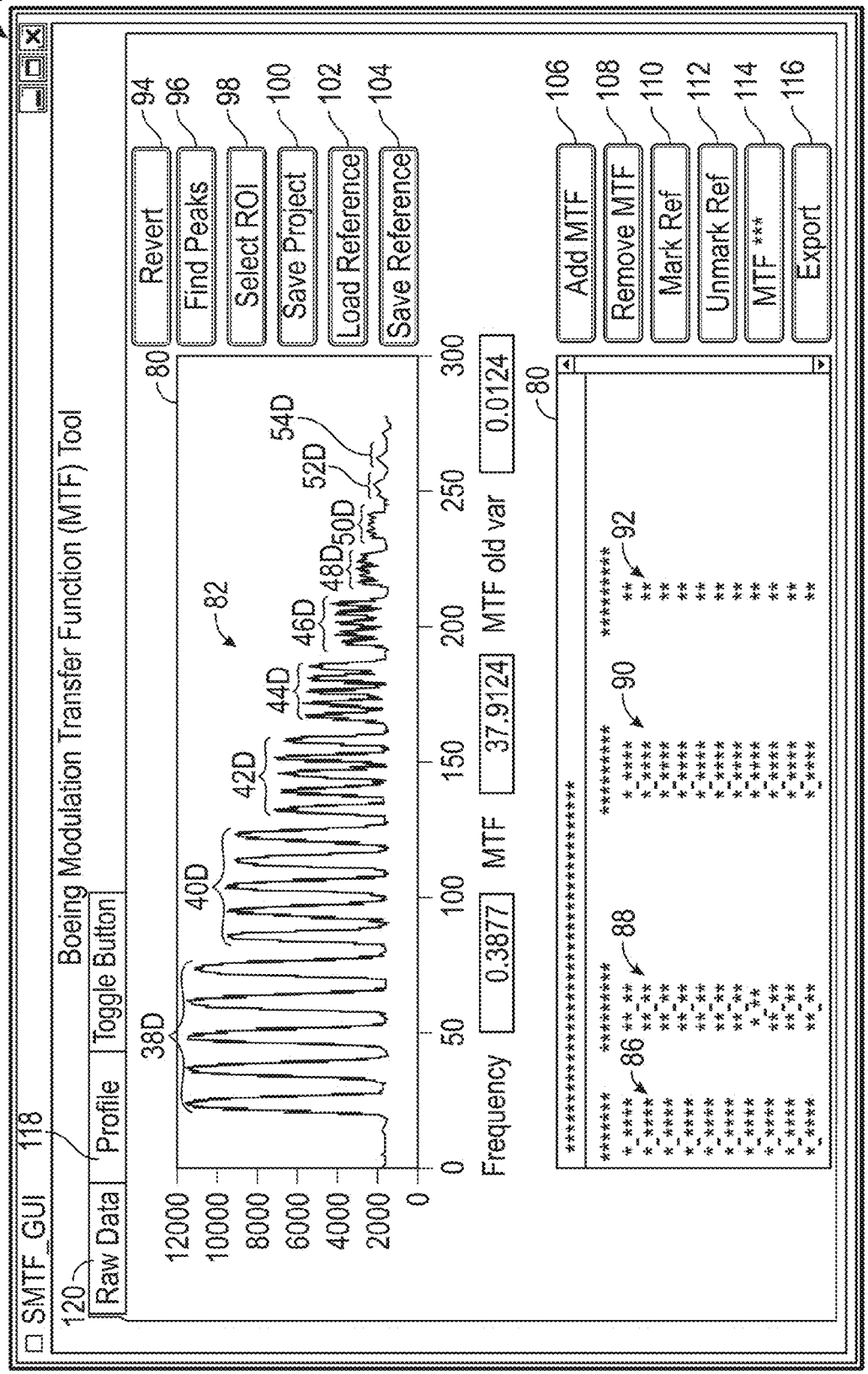
FIG. 6 is a display of the line profile and peak-to-peak data displayed on the graphical user interface of FIG. 5.

As shown in FIG. 6, the user interface 16 may be configured to show a screenshot that includes an image 80 of a line profile 82 representing photon counts of the backscatter images of, for example, the image 74 in FIG. 3. The line profile 82 thus shows the photon counts for the x-ray backscatter from rods 36 of group 38 (FIG. 2) as the peaks 38D, the photon counts for group 40 as peaks 40D, and so on for groups 42-54 as peaks 42D, 44D, 46D, 48D, 50D, 52D, and 54D, respectively. The line profile 82 thus shows the ability of the detectors 18, 20 (either singly or in combination) to distinguish the individual rods for the groupings of rods of progressively decreasing thickness. From the graph line profile 82, the photon counts progressively decrease from the thicker rod groupings 38, 40, 42, 44 (FIG. 2) and become less distinct in the groupings 46, 48, 50, 52, 54, as evidenced by their corresponding line profiles 38D-54D. Groups represented by curves 48D-54D may be considered indistinguishable.

Also as shown in FIG. 6, the GUI 16 may include peak-to-peak text data in display 84, listing frequency values 86, MTF frequencies 88, MTF standard deviations 90, and optionally, provide a reference number in column 92 for each value. The GUI 16 also may include virtual buttons that may be actuated by a mouse for switching from one image to another, such as button 94 for reverting the user interface, button 96 for finding the peaks on the line profile 82, button 98 for selecting a region of interest ("ROI") of the curve of the entire x-ray backscatter image of FIGS. 3-5, button 100 for saving the project in storage 76 (FIG. 1), button 102 for loading a reference image (such as the image of FIG. 3), and button 104 for saving the reference image.

The GUI 16 also may include a virtual button for adding an MTF 106, removing the MTF with button 108, marking the reference with button 110, unmarking the reference with button 112, adding an MTF point with button 114 and exporting the data with button 116. Further, the image shown in FIG. 6 may be selected by selecting the virtual tab 118 marked "Profile" at the top of the page. In contrast, the tab marked "Raw Data" 120 may be used to call up the images of FIGS. 3, 4 and 5.

Figure 7:
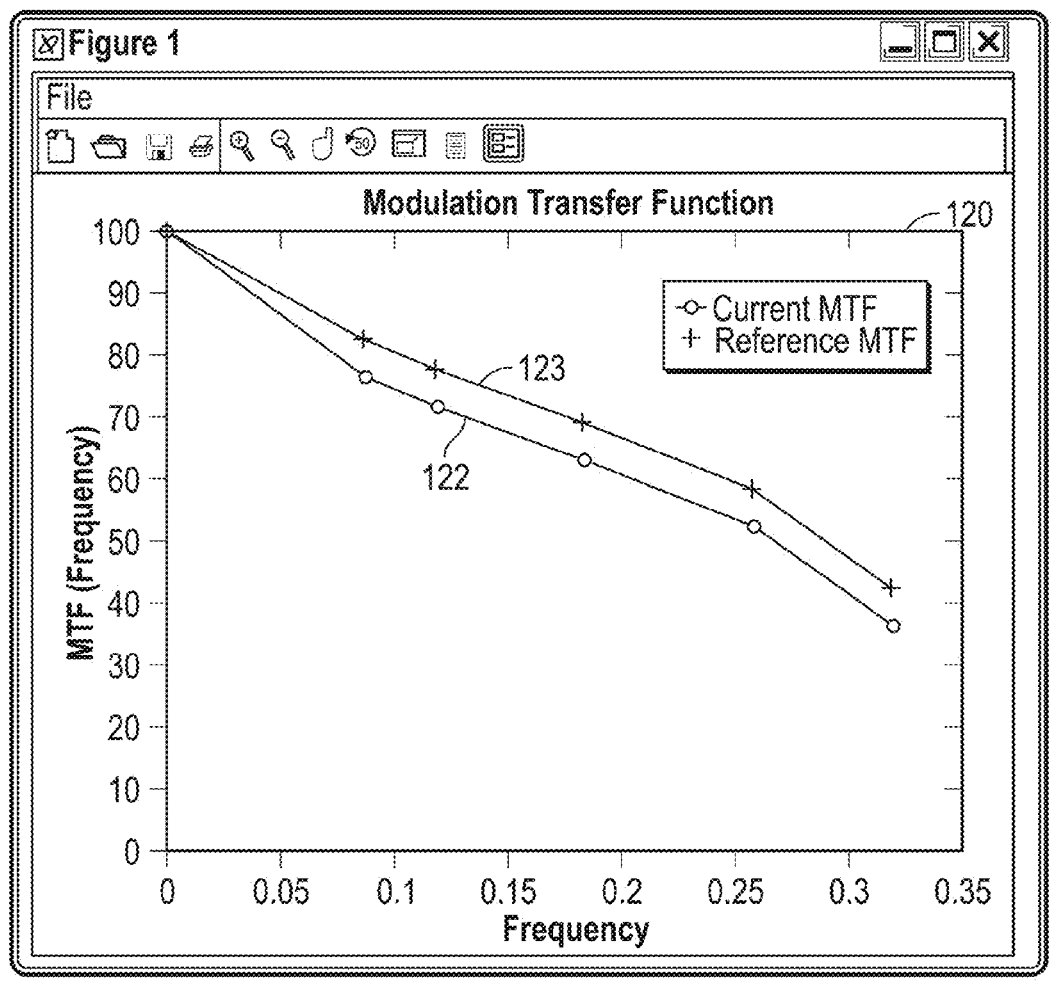
FIG. 7 is a display of the modulation transfer function plot of the line profile of the display of FIG. 6.

As shown in FIG. 7, the interface 16 may include a display 120 that may include a plot 122 of the current MTF displayed on the user interface of display 80 of FIG. 6. The plot 122 may be used to record, monitor and compare x-ray backscatter performance of the x-ray system being studied. In an embodiment, the MTF may be calculated by subtracting from the high average peak the low average peak, then dividing the difference by the sum of the high average peak and the low average peak: [(high average peak)−(low average peak)]/[(high average peak)+(low average peak)].

In an embodiment, the plot 122 may represent the MTF (frequency) on the Y-axis plotted against the frequency on the X-axis, taken from display 84 of the user interface shown in FIG. 6. The Y-axis is a scale from 1 to 100, with the 100 value representing the ratio of bright and dark signals from rods (e.g. rods 38 in FIG. 1) having the greatest thickness, shown as sine wave 38D in FIG. 6. The other points on plot 122 represent ratios for rods of other thicknesses, i.e., from sine waves 40D-48D in FIG. 6. The X-axis represents the frequency in terms of number of rods per unit width, so as the rods decrease in thickness, the frequency of rods per unit width increases. This plot 122 may be used to record, monitor, and compare x-ray backscatter system performance. In an embodiment, the display 120 also may be used to show a plot 123 of a reference MTF on the user interface of display 80 of FIG. 6.

The reference MTF plot 123 may be kept in storage 76 (FIG. 1) of readings of the system 10 taken as initial readings when the system has been adjusted and when all components are properly calibrated. As shown in FIG. 7, current MTF plot 122 shows that the system 10 has degraded slightly from the reference settings, because the curve shows slightly lower values at each frequency.

Figure 8:
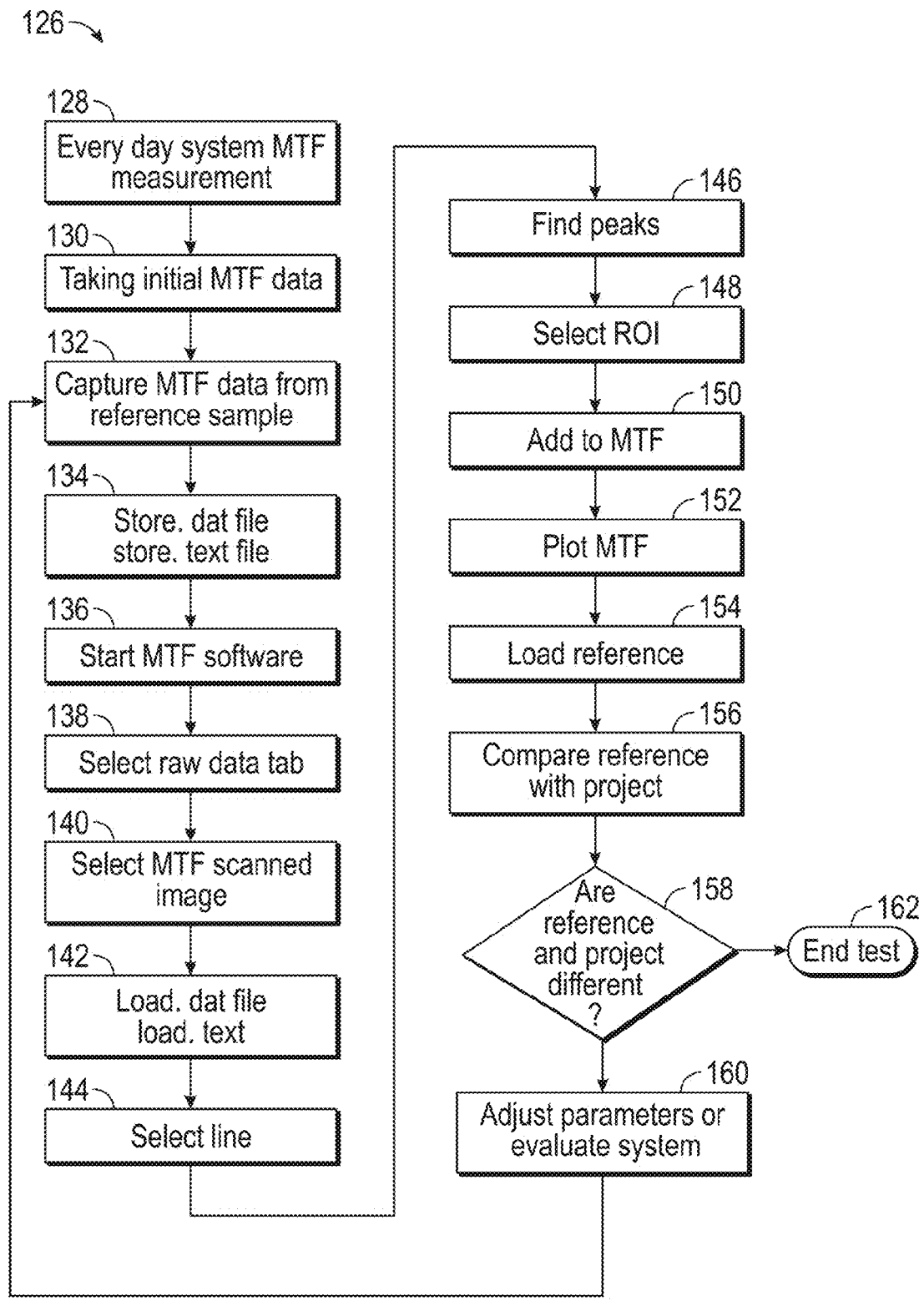
FIG. 8 is a flowchart of the method for quantifying x-ray backscatter system performance performed by the system of FIG. 1.

As shown in FIG. 8, the process for testing a x-ray backscatter system 10 using the reference standard 12 and user interface 16 is shown at 126. As shown in step 128, an everyday system MTF measurement is taken using the reference standard 12 and user interface 16 (FIG. 1). As indicated in block 130, the initial data is taken, and in step 132 the MTF data is captured from the reference sample, such as the image in FIG. 3. This information is stored in storage 76, as indicated at step 134 as a data file and/or a text file. The MTF software is then loaded, as indicated at step 136 and the raw data tab 120 (FIG. 6) is selected, as indicated at step 138.

As indicated at step 140, an MTF scanned image, such as the image of FIG. 4, may be selected, and, as indicated at step 142, the photon counts may be stored in a data and/or text file.

As indicated at step 144, a region of interest (ROI) or line segment may be selected to yield a line profile 82 of display 80 of FIG. 6. In the next step, indicated at 146, the peaks of the line profile are found by actuating the find peaks button 96 on the display of FIG. 6. In step 148, the ROI is selected and added to the MTF, as indicated at step 150. As indicated in step 152, the MTF 15 plotted, yielding a plot such as plot 122 of display 120 of FIG. 7.

As indicated at step 154, the reference is loaded and a comparison is made between the reference plot and the plot from the selected scanned image taken at step 140, as indicated at step 156. As indicated at decision diamond 158, if the reference plot and the test plot are different, then, as indicated at step 160 the system parameters are adjusted, or the system evaluated to determine the reason for disparity. In the alternative, as indicated at block 162, if the reference plot and the project plot are the same; that is, they coincide, as shown in FIG. 7, the test is completed.

The disclosed system and method for quantifying x-ray backscatter performance solves the problem of the need for measuring, tracking and comparing the imaging capability of x-ray backscatter systems. The system and method may achieve this by their ability to resolve small features with adequate image contrast. Spatial frequency response of an imaging system is the contrast at a given spatial frequency. Spatial frequency may be measured in cycles or line pairs per millimeter (lp/mn), which is analogous to cycles per second (Hz) in audio systems. Lp/mn, or cycles per pixel (c/p) or line widths per picture height (LW/PH) can all be used. High spatial frequencies correspond to fine image detail. The response of imaging system components tends to roll off at high spatial frequencies (i.e., smaller features). High spatial frequencies correspond to fine image detail. The more extended the response, the finer the detail and the sharper the image.

The disclosed system and method utilizes a special reference standard in the form of the standard 12, and a modulation transfer function ("MTF") that enables the performance of x-ray backscatter systems to be quantified, and thus compared against a reference standard. Variations in backscatter x-ray intensity across the image of the standard are quantified and displayed on the user interface 16.

As shown in FIGS. 9A and 9B, the system 10 (see FIG. 1) may be utilized with an x-ray tube 200, in place of x-ray tube 22, having an aperture 202 that may emit an x-ray field of view 204. The x-ray tube 200 may be positioned within an enclosure in the form of aperture wheel 206 having a generally cylindrical housing 208 that may enclose the x-ray tube partially or completely. The aperture wheel 206 may have a plurality of spokes 210, 212, 214, 216, 218 projecting radially outward from the housing 208. Each of the spokes 210-218 may have a hollow interior passage 220, 222, 224, 226, 228, respectively. The hollow interior passages 220-228 may be positioned to be rotated into registration with an opening 230 in the housing 208 that allows a collimated x-ray beam 232 from the x-ray tube 200 to exit the aperture wheel 206.

In an embodiment, each of the spokes 210-218 may include an adjustable aperture 234, 236, 238, 240, 242, respectively, mounted on an end of the spoke and in communication with the respective hollow interiors 220-228. As will be discussed, the adjustable apertures 234-242 may be selectively adjusted by an operator, or selectively adjusted automatically, to vary the shape and/or size of the opening, which may shape the collimated x-ray beam 232, as well as vary the flux or intensity of the x-ray beam 232 exiting the spokes 210-218. In an embodiment, only one of the apertures 234-242 may be adjustable, and the remaining apertures may be fixed; that is, the remaining apertures may be fixed and non-adjustable in the size of their respective openings.

The aperture wheel 206 may include a motor drive 244 that may be connected by a drive linkage 246 to rotate the spokes 210-218 to bring successive spokes into registry with the opening 230 to perform a raster scan of an object 247 (FIG. 10) to be inspected.

Figure 10:
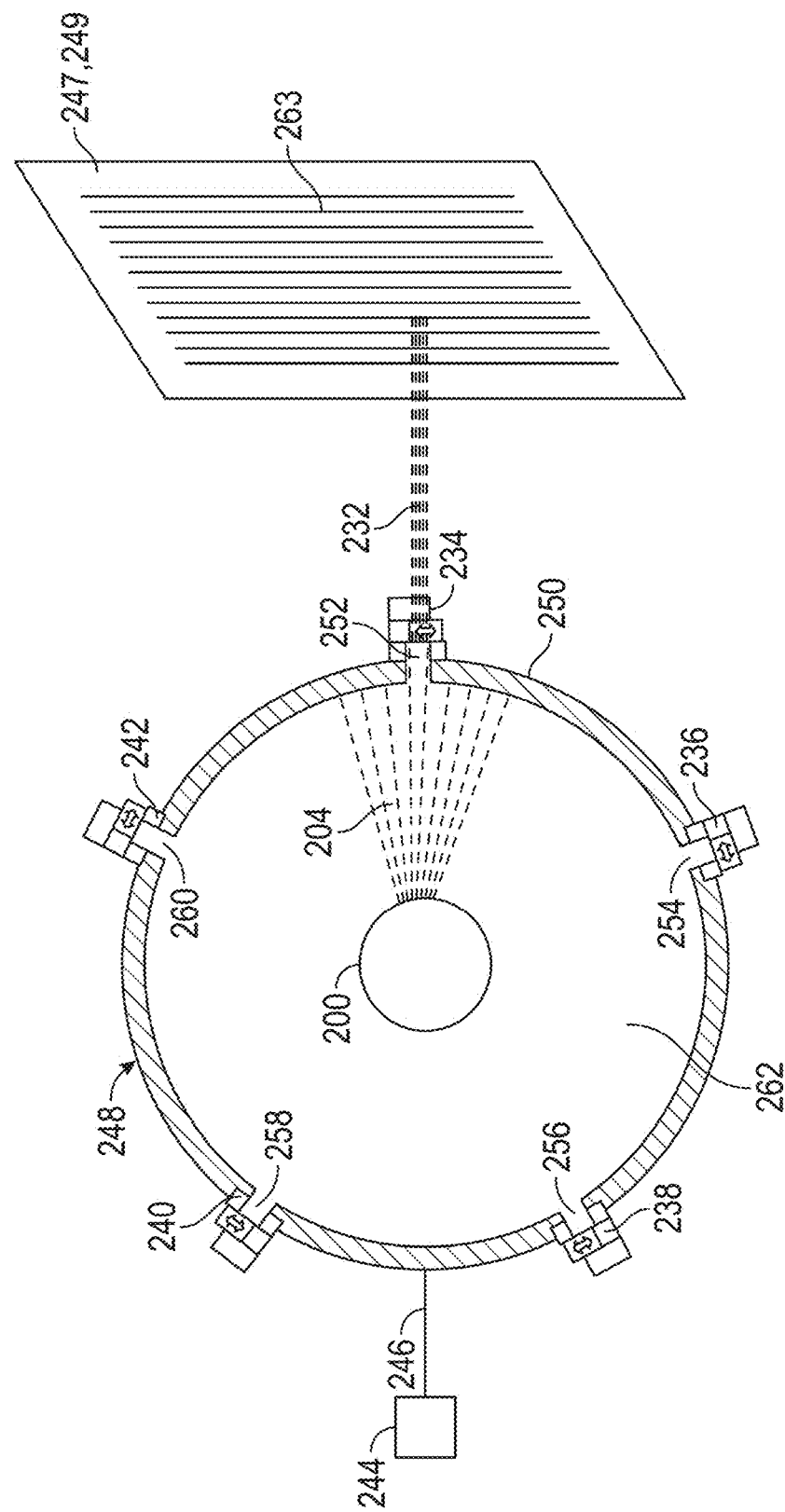
FIG. 10 is a side elevation in section of another embodiment of an aperture wheel having the disclosed adjustable apertures.

As shown in FIG. 10, in another embodiment, the x-ray tube 200 may be located and wholly or partially enclosed within an enclosure in the form of an aperture wheel enclosure 248 having adjustable apertures 234, 236, 238, 240, and 242. The adjustable apertures 234-242 may be mounted directly on the housing 250, rather than on the ends of spokes 210-218 as shown in FIGS. 9A and 9B. The housing 248 may include openings 252, 254, 256, 258, 260 that may be in registration with the adjustable apertures 234-242 mounted on the housing to allow a collimated x-ray beam 232 to exit the enclosure 248 from the interior 262 of the enclosure 248. In the embodiments of FIGS. 9A, 9B and 10, the x-ray beam 232 may be collimated and result from the x-ray field 204 emanating from the x-ray tube 200. The enclosure 248 may take the form of a wheel similar in design and operation to the aperture wheel 208 of FIGS. 9A and 9B.

The housing 250 may be driven by a motor 244 through a mechanical linkage 246 to rotate to bring the adjustable apertures 234-242 successively into alignment with the x-ray field of view 204, so that collimated x-ray beams 232 may successively emanate from the adjustable apertures 234-242. The motor 244 may be actuated to rotate the enclosure 248 to perform raster scans 263 on the object 247. In embodiments, the object 247 may be a body panel or a structural member of a vehicle 249, such as an aircraft, a spacecraft, a land vehicle, or a marine vehicle. In specific embodiments the object 247 may be a section of skin of a fuselage or of a wing of a vehicle 249 such as an aircraft, and may include rivets. The x-ray backscatter from the raster scans 263 may be measured by detectors 18, 20 (see FIG. 1) associated with the x-ray tube 200 and stored in storage 76 and/or displayed on a GUI 16 of display 14.

Figure 11:
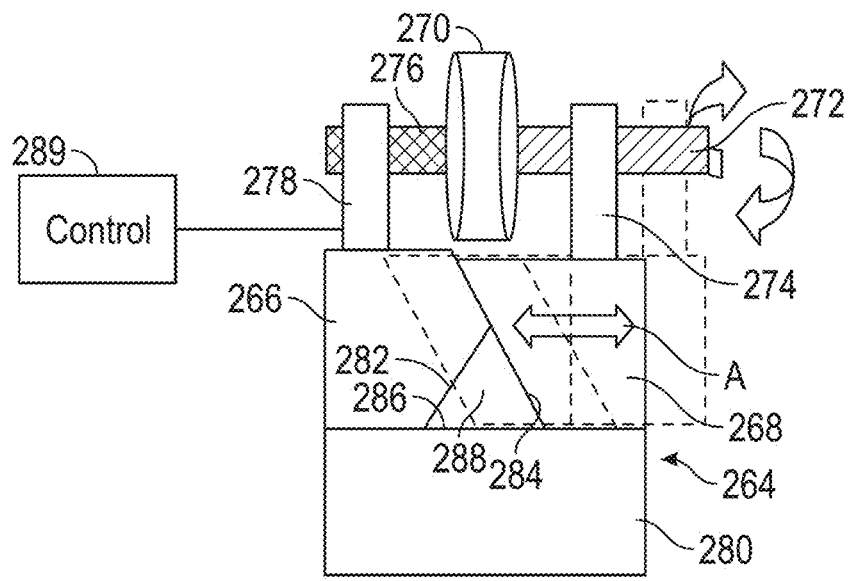
FIG. 11 is a detail showing an embodiment of the disclosed adjustable aperture.

As shown in FIG. 11, an exemplary adjustable aperture 264 may include two flat, plate-shaped shutters 266, 268 that may be positioned by a motor 270, which in embodiments may be a small electric motor or a nanomotor. The motor 270 may be connected to drive, or include, a threaded shaft 272 that threads into a boss 274 that may be connected to the shutter 268. The motor 270 may be mounted on a fixed support, such as fixed shaft 276, that may be held in place by a boss 278 attached to the fixed shutter 266, or in an embodiment, to adjacent fixed structure such as the aperture wheel 248 (FIG. 10), or a spoke 210-218 (FIG. 9A). The two shutters 266, 268 may slide against an aperture wall segment 280 of the end of, for example, the spoke 210-218 of the enclosure 206 of FIGS. 9A and 9B, or may be a portion of the enclosure 248 of FIG. 10. Alternatively, the adjustable aperture may be mounted on an end of x-ray tube 22 (FIG. 1).

In one particular embodiment, each of the shutters 266, 268 may be in the shape of a parallelogram. The shutters 266, 268 may be positioned in partially overlapping relation to each other, having straight sides 282, 284 that are oriented at an angle of approximately 60° relative to each other, and at an angle of approximately 60° to the adjacent straight side 286 of the segment 280 of the housing 208, 248 of the aperture wheel 206, 248. As a result of this orientation, the opening 288 formed by the edges 282, 284, 286 may maintain the same shape, which in an embodiment may be an equilateral triangle, even as the shutter 268 is moved to the left or right as indicated by the arrow A in FIG. 11 relative to shutter 266 and to wall segment 280.

Movement of the shutter 268 to the left in FIG. 11 in the direction of arrow A by the motor 270 may cause the opening 288 to decrease in size, but maintain its shape of an equilateral triangle. Conversely, movement of the shutter 268 to the right in the direction of arrow A by motor 270 may cause the opening 288 to increase in size (i.e. cross-sectional area) while maintaining its shape, which in this embodiment is an equilateral triangle shape. Movement of the shutter 268 relative to fixed shutter 266 and wall segment 280 to vary the size of the opening 288 in this fashion may result in increasing or decreasing the flux or intensity of the x-ray beam 232 emanating from the aperture wheel 208, 248.

Actuation of the motor 270 to vary the size of the opening 288 may be effected by a computer control 289, which in embodiments also may actuate the motor 244 to cause the x-ray tube 200 and enclosure 206, 248 to perform raster scans on the object 247. In embodiments, the control 289 may actuate the motor 270 on the fly; that is, during a raster scans 263 (FIG. 10), to vary the x-ray flux in the x-ray beam 232 directed at the object 247 being inspected. In other embodiments, the x-ray tube 200 and enclosure 206, 248 may be actuated by motor 244 to complete raster scans 263 of an area on the object 247 at one aperture size, for example an aperture 288 having an average width of 2 mm.

The control 289 then may actuate the motor 270 to adjust the size of the opening 288 of the adjustable aperture 264 to a smaller area, for example an opening having an average width of 0.5 mm. The motor 244 then may actuate the aperture wheel 206, 248 to perform a second, subsequent raster scan 263 of that same area of the object 247 using more scan lines than the previous scan and at a lower x-ray flux or intensity, which may provide a higher resolution, higher contrast scan to be detected by detectors 18, 20 (FIG. 1). In an embodiment, the control 289 may actuate the motor 270 to decrease the average width of the opening 288 further, for example to 0.25 mm, and the control 289 actuate the motor 244 to cause the x-ray tube 200 and enclosure 206, 248 to perform a third, subsequent raster scan 263 of that same area of the object 247 using more scan lines than the previous scan and at still lower an x-ray flux or intensity, which may provide an even higher resolution scan than the two previous scans.

This procedure may be desirable in a process wherein the first scan 263 of the object 247 may find an anomaly on or in the object, which may be found by the detectors 18, 20 receiving the x-ray backscatter, and shown on GUI 16 of display 14. Then, the x-ray tube 200 may be directed by motor 244 and configured by control 289 to perform subsequent scans 263 of the anomaly on the object 247 at increasingly higher resolutions (i.e., using apertures 288 made successively smaller by motor 270). The successive scans 263 may be performed using a single adjustable aperture, such as the adjustable aperture 264 shown in FIG. 10, which may be adjusted during or after each raster scan 263. Alternatively, the successive scans 263 may be performed using two or more multiple adjustable apertures 234-242 mounted on, for example, the spokes 210-218 of aperture wheel 206, or aperture wheel 248, wherein the adjustable apertures may be adjusted on the fly to openings 288 of successively smaller areas.

Figure 12:
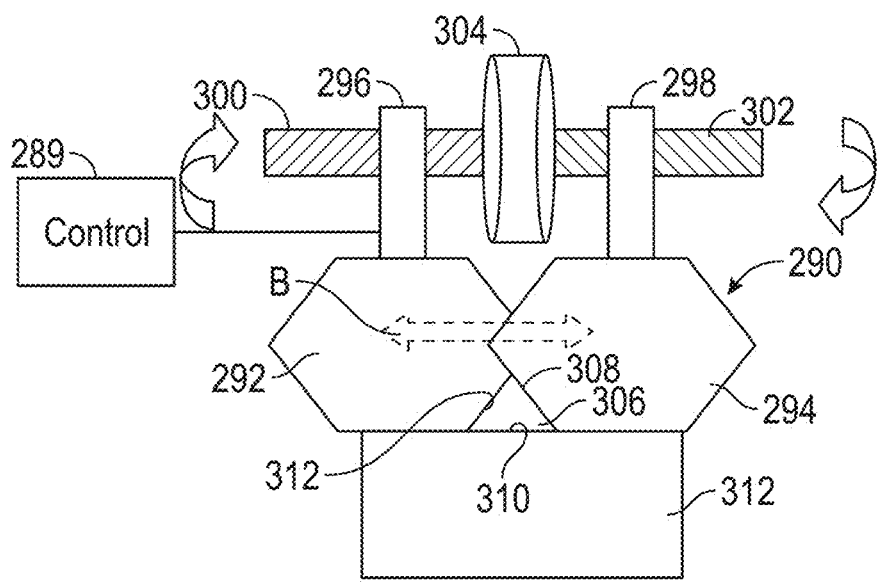
FIG. 12 is a detail showing another embodiment of the disclosed adjustable aperture.

As shown in FIG. 12, an adjustable aperture 290 may be configured to have two flat, plate-shaped moving shutters 292, 294, each having a projecting boss 296, 298 that is engaged with a respective threaded shaft 300, 302 operably connected to a motor 304, which may be a nanomotor. In embodiments, the motor 310 may be fixed to the spoke 210-218, or to the enclosure 248, or the shafts 302 may be reverse threaded and/or counter-rotated by the motor 304. The motor 304 may be actuated by an operator to selectively move the shutters 292, 294 in the direction of arrow B to increase or decrease the size of the opening 306.

In an embodiment, shutter 294 may include an edge 308 that is positioned at a 60° angle to the edge 310 of an adjacent portion of the wall 312 of the end of a spoke 210-242 (FIG. 9A), for example, and shutter 292 may include an edge 312 that is oriented at a 60° angle to the edge 310, and with respect to edge 308. Thus, edges 308, 310, 312 may meet to form an equilateral triangle-shaped opening 306. Shutters 292, 294 may overlap so that actuation of the shafts 300, 302 by the motor 304 may cause the shutters to variably overlap each other as they move toward or away from each other in the direction of arrow B, either toward the center of the adjustable aperture 290, or away from the center of the adjustable aperture. An advantage of the adjustable aperture 290 of FIG. 12 over the adjustable aperture 272 of FIG. 11 is that the opening 306 remains centered relative to the apertures 252-260 of the aperture wheel 248 of FIG. 10, or with the hollow interiors 220-228 of the spokes 210-218 of the aperture wheel 208 of FIGS. 9A and 9B.

Figure 13A:
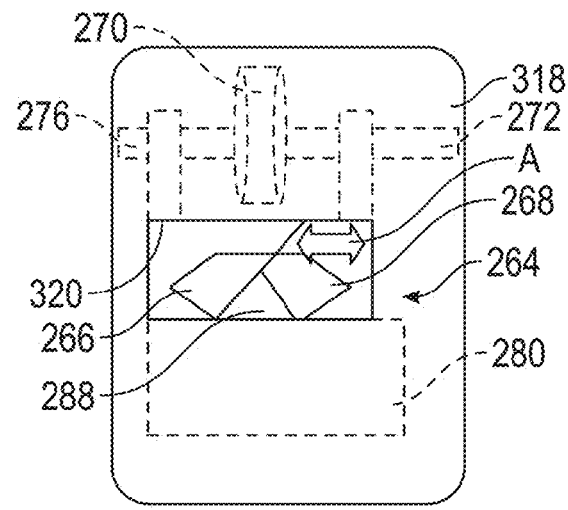
FIGS. 13A and 13B show a plan view and a side elevation, respectively, of the adjustable aperture of FIG. 12 mounted on an end of a spoke of the aperture wheel of FIGS. 9A and 9B.
Figure 13B:
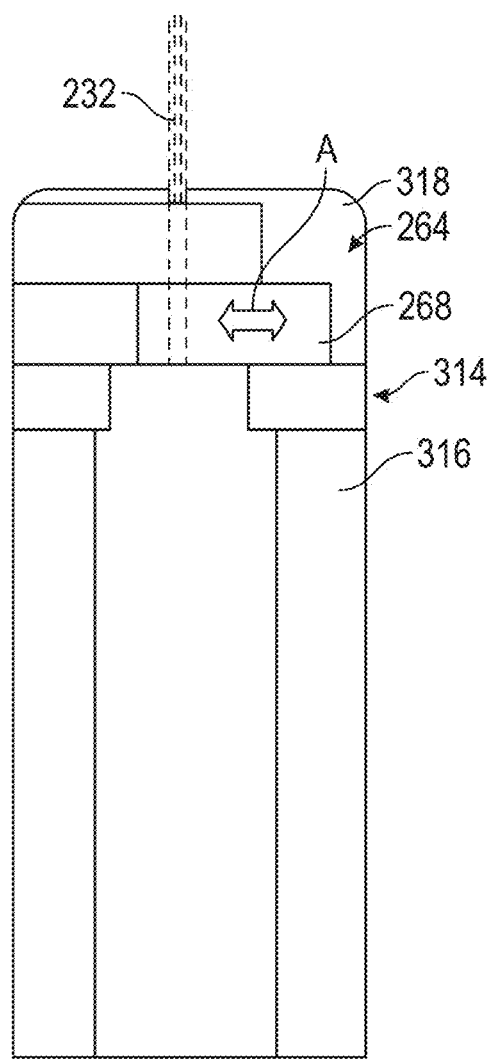

In a specific application of the adjustable aperture 264, as shown in FIGS. 13A and 13B, the aperture 264 may be mounted on an end 314 of a spoke 316, which may be one or more of the spokes 210-218 of FIGS. 9A and 9B. The end cap 318 may be attached to the spoke 316 by a suitable adhesive, pressing it into the spoke, or by mechanical fasteners such that it is removable from the spoke. The spoke 316 may include an end cap 318 having an opening 320 in registration with the opening 288 formed by the adjustable aperture 264. The end cap 318 may be shaped to cover and enclose the motor 270 and shafts 272, 276, and partially cover and enclose the shutters 266, 268. The opening 320 may be in registration with the opening 288 so that the collimated x-ray beam 232 may exit the spoke 316. The opening 320 may be shaped to equal or exceed the largest size of the opening 306 of the adjustable aperture 264.

Figure 14A:
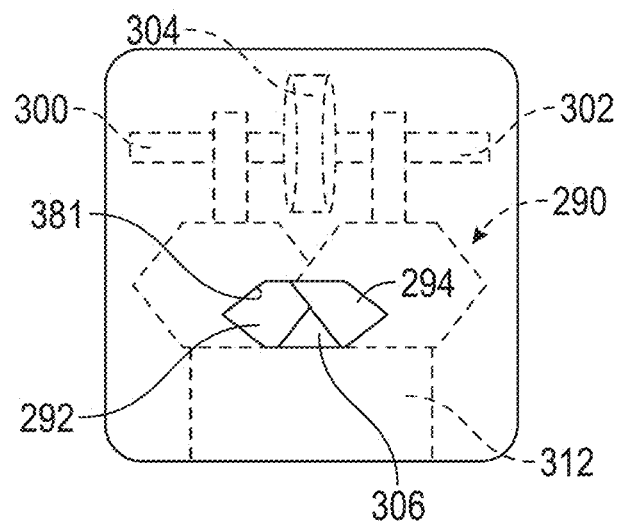
FIGS. 14A and 14B show a plan view and a side elevation, respectively, of another mounting arrangement of the adjustable aperture of FIG. 12, mounted on the end of a spoke of the aperture wheel of FIGS. 9A and 9B.
Figure 14B:
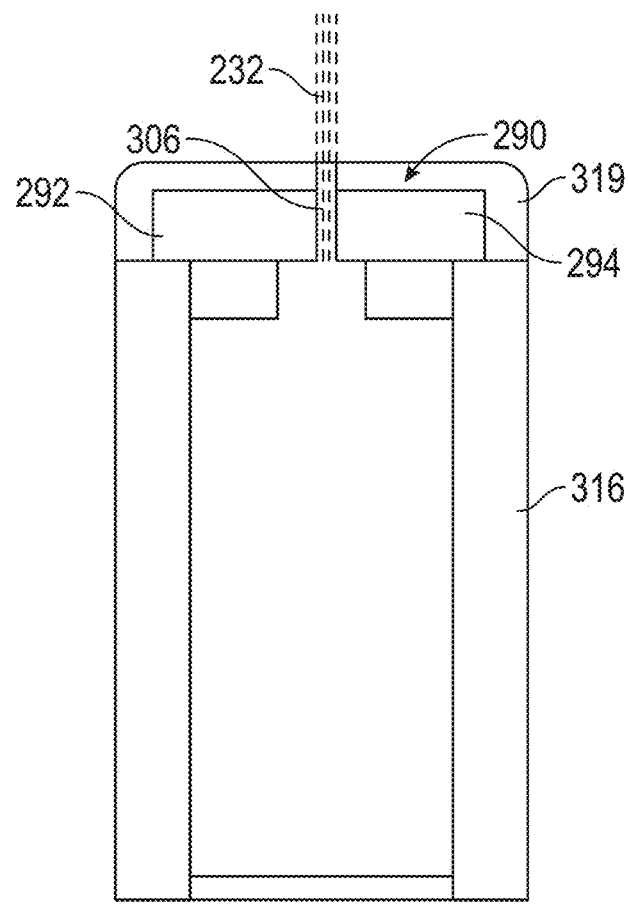
Figure 16A:
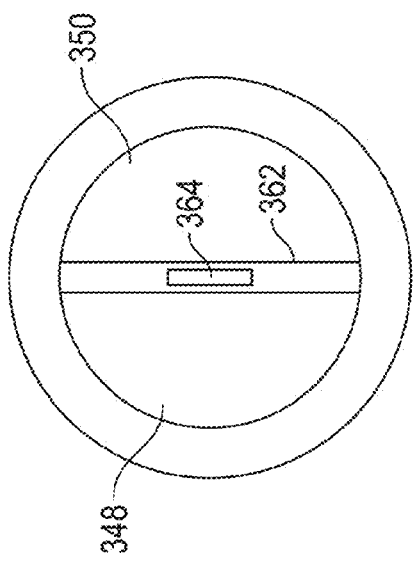
FIGS. 16A, 16B, 16C, and 16D show plan views of another embodiment of the disclosed adjustable aperture mounted in an end of a round collimator.
Figure 16B:
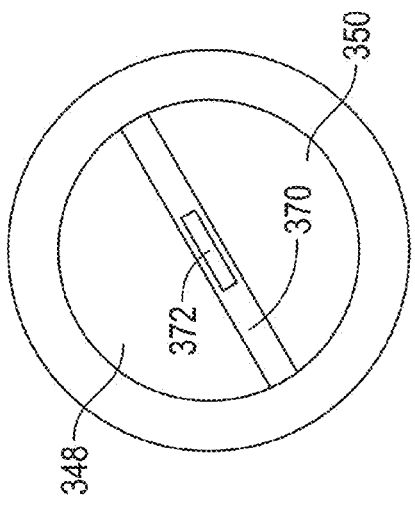
Figure 16C:
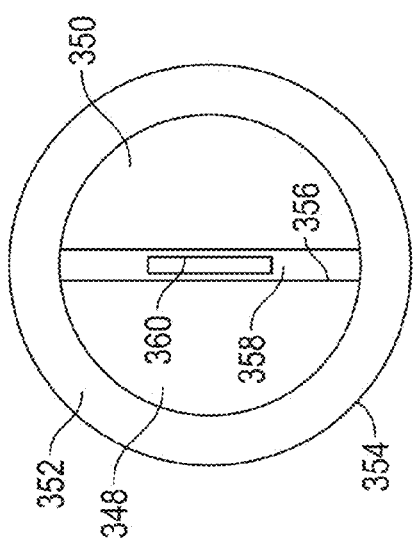
Figure 16D:
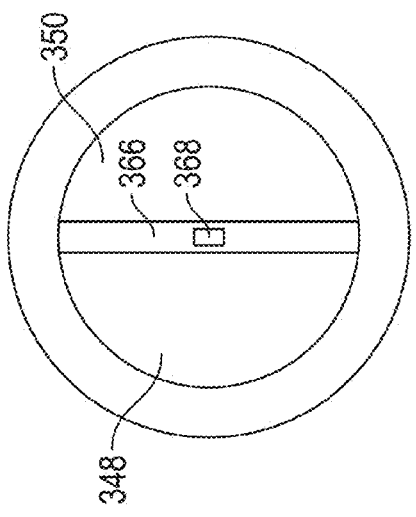

As shown in FIGS. 14A and 14B, a spoke 316 may include an end cap 319 shaped to cover and enclose the adjustable aperture 290. The end cap 319 may be attached to the spoke 316 by a suitable adhesive, pressing it into the spoke, or by mechanical fasteners such that it is removable from the spoke. The end cap 319 may include an opening 321 shaped and positioned to be in registration with the opening 306 formed by the adjustable aperture 290. The end cap 319 may partially cover not only the overlapping shutters 292, 294 but may completely cover the motor 304 and shafts 300, 302. In contrast to the end cap 318 of FIGS. 13A and 13B, where the opening 320 is offset from the center of the end cap to accommodate the shifting position of the opening 288 as the shutter 268 is moved in the direction of arrow A for adjustment of size, the opening 321 may be positioned substantially midway in the center of the end cap 290 because the opening 306 remains centrally located as the result of symmetrical movement of the overlapping shutters 292, 294 of the aperture 290.

As shown in FIGS. 15A, 15B, 15C, and 15D, in another embodiment, the adjustable aperture may include a pair of substantially flat, plate-shaped fixed shutters 322, 324 that may be pressed into the open end 332 of a square spoke 334. The shutters 322, 324 may be shaped and positioned on the open end 332 to form a gap 326 between them that may be filled partially with a flat shim 328, which also may be pressed into the open end 332. The shim 328 may have a slit 330 formed therethrough. In an embodiment, the shutters 322, 324 and shim 326 may be pressed into the open end 332 of a spoke 334 of, for example, an aperture wheel 206 (see FIG. 9A). In embodiments, the slit 330 may be oblong and generally rectangular, as shown in FIG. 15A. In other embodiments, the slit may be shorter, such as slit 336 of shim 338 in FIG. 15B, or almost square and relatively small, such as slit 340 of shim 342 in FIG. 15C. In other embodiments, the shutters 322, 324, and shims 326, 338, 342, 346 may be attached to the open end 332 by a suitable adhesive, by a mechanical connection, such as by screws, or by welding or brazing.

In yet another embodiment, the orientation of the slit 330, 336, 340 may be vertical or substantially vertical, as shown in FIGS. 15A, 15B, and 15C, or horizontal, as shown for aperture 344 of shim 346 in FIG. 15D, relative to the direction of raster scan 263. For inspections such as stress corrosion crack detection, there is a need for improved resolution along the linear scan direction. Smaller circular apertures may help, but as the aperture becomes very small, the whole is difficult and expensive to machine accurately, and also may limit the x-ray flux and therefore slow down a backscatter x-ray scan to a point where it may be impracticable to perform.

By providing the shims 328, 338, 342, and 346 with apertures 330, 336, 340, and 344, respectively, press fit into, or otherwise attached to, the ends 332 of spokes 334, the cost of manufacture is reduced and the design is simplified of the aperture wheel 206, 248. In addition, the slits 330, 336, 340, 344 may allow increased resolution, due to the narrow slit, but an increased flux due to the relatively wider opening, so scan speeds may remain high enough to be practicable. While vertical resolution may be reduced slightly, horizontal resolution, which is important for crack detection when their orientation is generally predictable, may be improved over prior art apertures having a uniform cross-section.

Similarly, as shown in FIGS. 16A, 16B, 16C, and 16D, the shutters 348, 350 may be substantially flat and plate-shaped, having a generally semi-circular shape. The shutters 348, 350 may be press-fitted into the open end 352 of a circular spoke 354 of an aperture wheel, such as the aperture wheel 206 shown in FIG. 9A, or aperture wheel 248 of FIG. 10. Such shutters 348, 350 may be shaped to form a gap 356 when pressed into or otherwise attached to the ends 352 of the spokes 354, and a shim 358 may be fitted between the shutters 348, 350 within the gap. The shim 358 may have an aperture 350 therethrough of a predetermined width and length, preferably having a length that may be a multiple of the dimension of the width to allow increased resolution, similar to slit 330 in FIG. 15A. Similarly, in FIG. 16B, shim 362 may have a slit 364, and in FIG. 16C, shim 366 may have a slit 368, and in FIG. 16D, shim 370 may have a slit 372. The orientation of the slit 372 in FIG. 16D may be at an angle to facilitate detection of a stress corrosion crack of a known or expected orientation.

Figure 17:
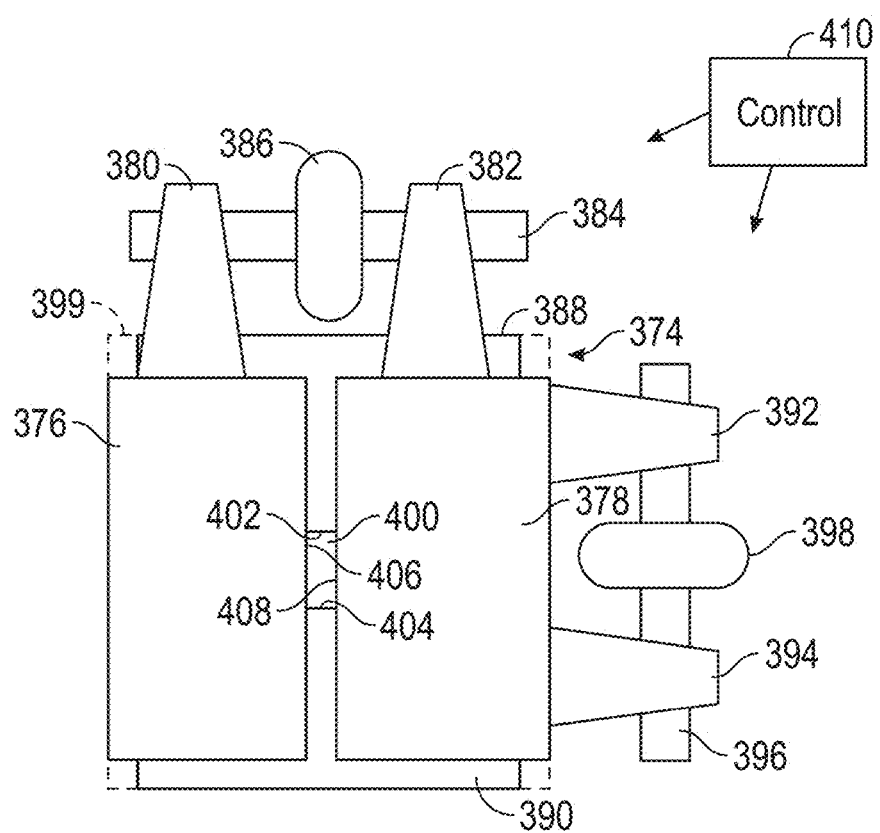
FIG. 17 shows a plan view of another embodiment of the disclosed adjustable aperture, in which nano motors position two sets of shutters.

As shown in FIG. 17, an adjustable aperture 374 may include an outer pair of substantially flat, plate-shaped shutters 376, 378 having bosses 380, 382, respectively, threaded into a threaded shaft 384 that may be rotated by a motor 386, which in embodiments may be a nanomotor. The adjustable aperture 374 also may include an inner pair of substantially flat, plate-shaped shutters 388, 390 including bosses 392, 394, respectively, threaded into a shaft 396 that may be rotated by a motor 398, which in embodiments also may be a nanomotor. The outer pair of shutters 376, 378 and inner pair of shutters 388, 390 may be mounted on an end 399 of a spoke 316 (FIG. 14B) of an aperture wheel 206 (FIG. 9A), or mounted on aperture wheel 248. The shafts 384, 396 may be threaded such that, when rotated by the motors 386, 398, respectively, the outer shutters 276, 378 and inner shutters 380, 382 each move toward each other or away from each other. The motors 386, 398 likewise may be attached to the end 399 of the spoke 316.

The inner pair of shutters 388, 390 may be oriented at an angle relative to the outer pair of shutters 376, 378, and in a particular embodiment may be oriented at a 90° angle to the shutters 376, 378. The outer pair of shutters 376, 378 may be positioned adjacent the inner pair of shutters 388, 390, and in an embodiment immediately behind them, to form with them a slit 400 that may be defined by an edge 402 of shutter 388, an edge 404 of shutter 390, an edge 406 of shutter 376, and an edge 408 of shutter 378. The motors 386, 398 may be actuated by a control 410, which also may actuate motor 244 (FIGS. 9A and 10) so that the motors 386, 398 may displace the panels 376, 378 relative to each other, and panels 388, 390 relative to each other, so that the shape and open area of the aperture 400 may be varied as desired. Further, this adjustability of the aperture opening may be effected during a scan, if desired. The adjustable aperture 374 may be mounted on an end of a spoke, such as one or more of the spokes 210-218 in FIG. 9A, or mounted on the aperture wheel 248 of FIG. 10. In another embodiment, a single adjustable aperture 374 may be mounted on an end of x-ray tube 22 (FIG. 1).

Figure 18A:
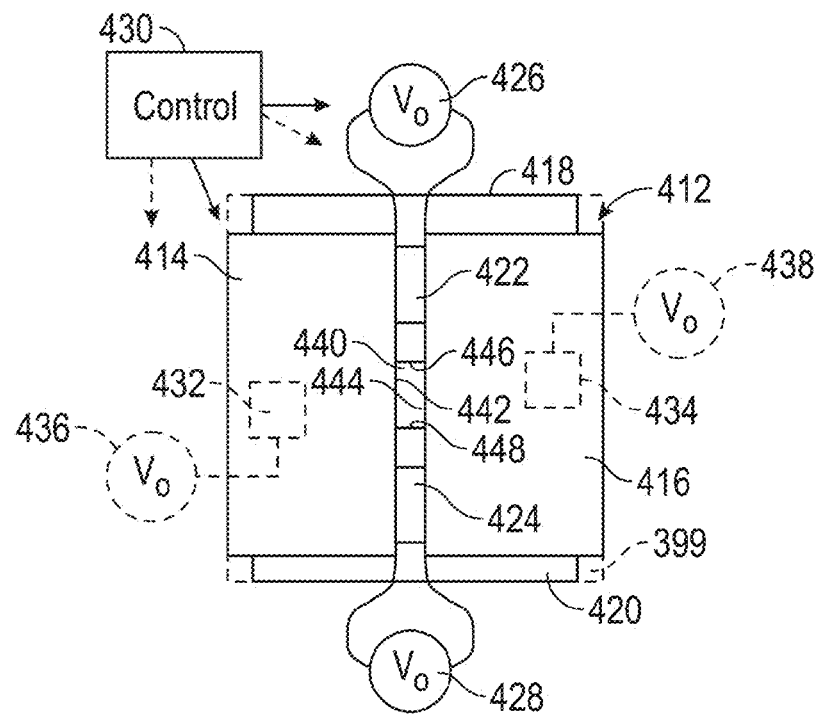
FIGS. 18A and 18B show plan views of another embodiment of the disclosed adjustable aperture, in which piezoelectric elements position two sets of shutters.
Figure 18B:
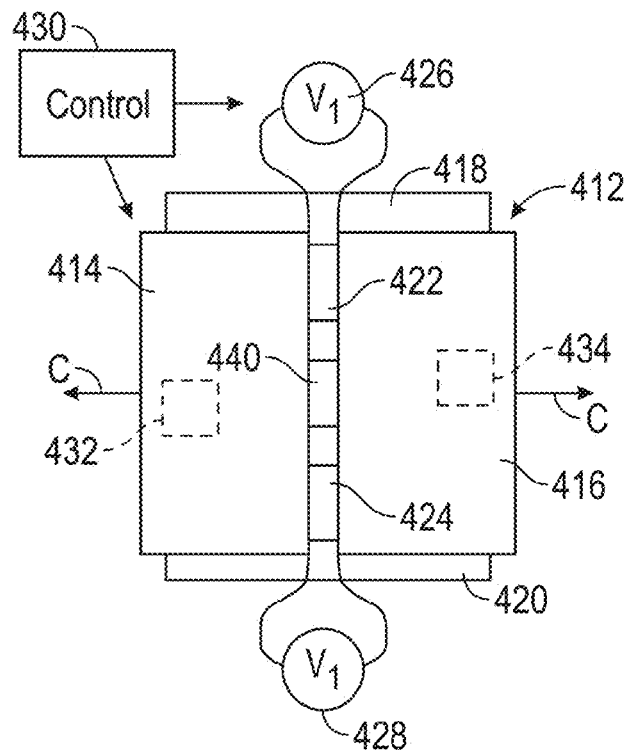

As shown in FIGS. 18A and 18B, in another embodiment, adjustable aperture 412 may include an outer pair of adjustable shutters 414, 416, and an inner pair of adjustable shutters 418, 420, which may be mounted on an end 399 of a spoke 316 of an aperture wheel 206 or the x-ray tube 22, or mounted on aperture wheel 248. Shutters 414, 416 may be attached to piezoelectric actuators 422, 424 that are connected to voltage sources 426, 428. The voltage sources 426, 428 may be actuated by a control 430 so that the spacing between the shutters 414, 416 may be varied by actuating the piezoelectric actuators 422, 424. In an embodiment, a second pair of piezoelectric actuators 432, 434 may be attached to and positioned between shutters 418, 420. Piezoelectric actuators 432, 434 may be actuated by voltage sources 436, 438 controlled by control 430. Thus, piezoelectric elements 422, 424 may control the shape, size, and aspect ratio of the slit aperture 440, which may be defined by edge 442 of shutter 414, edge 444 of shutter 416, edge 446 of shutter 418, and edge 448 of shutter 420.

As shown in FIG. 18B, actuation of piezoelectric elements 422, 424 by control 430 may cause the shutters 414, 416 to move in the direction of arrows C, thus increasing the width of the slit 440 of the aperture 412. Similarly, control 430 may actuate voltage sources 436, 438 (shown in FIG. 18A) to activate piezoelectric elements 432, 434 to move shutters 418, 420 toward or away from each other to vary the shape of the slit 440. This actuation of piezoelectric elements 422, 424, 432, 434 may be done selectively and without removing the aperture 412 from the x-ray tube 22 or aperture wheel 206, 248 on which it is mounted. Further, the control 430 may be programmed to vary the shape (including the aspect ratio) of the slit 440 in a pre-programmed fashion.

Thus, with the embodiment of FIGS. 18A and 18B, a slit type adjustable aperture 412 may be adjustable on the fly using piezoelectric materials. The piezoelectric materials may expand or contract based upon an applied voltage across selected crystal orientations. This structure and associated method may be used for the adjustable apertures shown in FIGS. 9A-17 as well.

The adjustable apertures 234-242, 264, 290, 326, 338, 342, 346, 358, 362, 366, 370, 374, and 412 shown in FIGS. 9A-18B preferably are made of tungsten. These adjustable apertures and associated method provide an improved set of adjustable apertures for an x-ray backscatter system that controls the size and shape of the x-ray beam that is rastered across the target structure 247 during a raster scan 263. These adjustable apertures may improve system performance by providing options beyond the standard circular opening of selected size machined into tungsten. These apertures may be adjustable to reduce the need for multiple sets of apertures, each of a different, fixed size, and can provide improved resolution of defects in selected directions without sacrificing flux or scan speed.

These disclosed adjustable apertures may be adjusted, either using the motors 270, 304, 386, 398, or by replacing the shims 328, 338, 342, 346, 358, 362, 366, and 370 to provide an opening that may be very small, on the order of 0.25 mm or 0.5 mm in width in order to detect small cracks such as stress corrosion cracks. At the same time, and if desired, on the fly, the adjustable apertures may be adjusted to have a larger aperture that allows for general scanning at higher flux levels, which enables higher scan speeds. This can be done without replacing the entire aperture to achieve the desired size. The adjustable apertures eliminate the need for software normalization to achieve consistent x-ray backscatter flux intensity. Further, the orientation of the apertures may be selected such as the apertures 344, 372 in FIGS. 15B and 16B, or may be adjusted, such as the adjustable aperture 374 of FIG. 17 and the adjustable aperture 412 of FIGS. 18A and 18B to provide improved crack detection that results from orienting the wide dimension of the aperture perpendicular aperture. Other orientations of the aperture relative to the predicted crack orientation may be selected to improve the image resolution and defect detection.

While the methods and forms of apparatus herein described constitute preferred embodiments of the disclosed system and method for quantifying x-ray backscatter system performance, it is to be understood that variations may be made therein without departing from the scope of the invention.

What is claimed is:

1. An x-ray backscatter system, the system comprising:
   an x-ray tube for emitting an x-ray field;
   an enclosure that is an aperture wheel that surrounds the x-ray tube, the enclosure defining an end and an aperture mounted on the end of the enclosure, wherein the x-ray field exits the enclosure through the aperture; and
   a plurality of shutters that define an opening of the aperture, wherein one or more shutters of the plurality of shutters are moveable to vary at least one of a size and a shape of the opening, and wherein movement of the one or more shutters vary an amount of x-ray flux that exits the enclosure.

2. The x-ray backscatter system of claim 1, wherein the aperture is selected from a variably overlapping stationary shutter and movable shutter, a pair of variably overlapping movable shutters, and a variably adjustable slit aperture.

3. The x-ray backscatter system of claim 2, wherein the adjustable slit aperture is adjustable by one or both of mounting selected one of a plurality of shims of different widths and thicknesses on the aperture, and by selectively adjusting gaps between the plurality of shutters by motors.

4. The x-ray backscatter system of claim 1, wherein the plurality of shutters comprise a first pair of movable shutters and a second pair of moveable shutters disposed adjacent the first pair of shutters and oriented at a 90 degree angle relative to the first pair of shutters.

5. The x-ray backscatter system of claim 4, wherein the first pair of movable shutters are attached to a first piezoelectric actuator and the second pair of movable shutters are attached to a second piezoelectric actuator, wherein the first piezoelectric actuator is connected to a first voltage source and the second piezoelectric actuator is connected to a second voltage source.

6. The x-ray backscatter system of claim 5, further comprising a control system in communication with the first and second voltage sources for independently controlling the first voltage source to move the first pair of shutters and for independently controlling the second voltage source to move the second pair of shutters to vary the size of the aperture.

7. The x-ray backscatter system of claim 1, wherein the enclosure further comprises a plurality of spokes, wherein each of the plurality of spokes are spaced apart around a periphery of the aperture wheel.

8. The x-ray backscatter system of claim 7, wherein each of a plurality of apertures are disposed at an end of each of the plurality of spokes.

9. A method for producing x-ray backscatter, the method comprising:
   emitting an x-ray field using an x-ray tube;
   surrounding the x-ray tube with an enclosure, wherein the enclosure defines an end and an aperture mounted on the end of the enclosure, and wherein the x-ray field exits the enclosure through the aperture;
   partially blocking the x-ray field with the aperture, wherein the enclosure is provided in the shape of a wheel, and wherein each aperture of a plurality of apertures are spaced apart along a periphery of the wheel; and
   moving one or more shutters that are part of a plurality of shutters to vary an amount of x-ray flux through an opening of the aperture, wherein the one or more shutters move to vary at least one of a size and a shape of the opening.

10. The method of claim 9, further comprising rotating the enclosure in the shape of the wheel to perform a raster scan.

11. The method of claim 10, wherein rotating the enclosure in the shape of the wheel to perform a raster scan further comprises aligning each of the plurality of apertures with the x-ray tube.

12. The method of claim 9, wherein varying the amount of x-ray flux through the aperture further comprises adjusting the aperture using one of a variably overlapping stationary shutter and movable shutter, a pair of variably overlapping movable shutters, and a variably adjustable slit aperture.

13. The method of claim 9, wherein adjusting the aperture further comprises adjusting the adjustable slit aperture by one or both of mounting selected one of a plurality of shims of different widths and thicknesses on the aperture, and by selectively adjusting gaps between the plurality of shutters by motors.

14. The method of claim 9, wherein partially blocking the x-ray field with the enclosure further comprises providing a plurality of spokes, wherein each of the plurality of spokes are spaced apart around the periphery of the aperture wheel.

15. The method of claim 9, wherein partially blocking the x-ray field with the enclosure further comprises providing each of the plurality of apertures at an end of each of the plurality of spokes.

16. The method of claim 9, wherein varying the amount of x-ray flux through the aperture further comprises moving a first pair of movable shutters and a second pair of moveable shutters disposed adjacent the first pair of shutters and oriented at a 90 degree angle relative to the first pair of shutters.

17. The method of claim 16, wherein varying the amount of x-ray flux through the aperture further comprises connecting the first pair of movable shutters to a first piezoelectric actuator and the second pair of movable shutters to a second piezoelectric actuator, wherein the first piezoelectric actuator is connected to a first voltage source and the second piezoelectric actuator is connected to a second voltage source.

18. The method of claim 17, wherein varying the amount of x-ray flux through the aperture further comprises controlling the first and second voltage sources with a control system to move the first pair and second pair of shutters to vary the size of the-aperture.

19. A method for producing x-ray backscatter, the method comprising:

emitting an x-ray field using an x-ray tube;

surrounding the x-ray tube with an enclosure, wherein the enclosure defines an end and an aperture mounted on the end of the enclosure, and wherein the x-ray field exits the enclosure through the aperture;

partially blocking the x-ray field with the aperture, wherein partially blocking the x-ray field with the enclosure further comprises providing a plurality of spokes, and wherein each of the plurality of spokes are spaced apart around a periphery of an aperture wheel; and moving one or more shutters that are part of a plurality of shutters to vary an amount of x-ray flux through an opening of the aperture, wherein the one or more shutters move to vary at least one of a size and a shape of the opening.

20. A method for producing x-ray backscatter, the method comprising:

emitting an x-ray field using an x-ray tube;

surrounding the x-ray tube with an enclosure, wherein the enclosure defines an end and an aperture mounted on the end of the enclosure, and wherein the x-ray field exits the enclosure through the aperture;

partially blocking the x-ray field with the aperture; and moving one or more shutters that are part of a plurality of shutters to vary an amount of x-ray flux through an opening of the aperture, wherein the one or more shutters move to vary at least one of a size and a shape of the opening, wherein varying the amount of x-ray flux through the aperture further comprises moving a first pair of movable shutters and a second pair of moveable shutters disposed adjacent the first pair of shutters and oriented at a 90 degree angle relative to the first pair of shutters.

* * * * *